United States Patent [19]

Matschiner

[11] Patent Number: 5,525,478
[45] Date of Patent: Jun. 11, 1996

[54] SOLUBLE THROMBOMODULIN-BASED ONE-STAGE ASSAY FOR VITAMIN-K DEPENDENT COAGULATION-INHIBITING PROTEINS

[76] Inventor: John T. Matschiner, 4015 Swanson Hall, University of Nebraska Medical Center, 600 S. 42nd St., Omaha, Nebr. 68198-8090

[21] Appl. No.: 481,185

[22] Filed: Jun. 7, 1995

Related U.S. Application Data

[63] Continuation of Ser. No. 771,644, Oct. 19, 1991, abandoned.

[51] Int. Cl.$^6$ ............... C12Q 1/56; C12Q 1/00; G01N 33/48
[52] U.S. Cl. ............... 435/13; 435/4; 435/69.6; 436/63; 436/69; 514/833
[58] Field of Search ............... 435/13, 69.6, 4; 514/83335; 436/63, 69

[56] References Cited

U.S. PATENT DOCUMENTS

| | | | |
|---|---|---|---|
| 4,736,018 | 4/1988 | Reutelingsperger | 514/2 |
| 4,748,156 | 5/1988 | Aoki et al. | 514/8 |
| 4,849,403 | 7/1989 | Stocker et al. | 435/24 |
| 5,001,069 | 3/1991 | Bartl et al. | 436/86 |
| 5,051,357 | 9/1991 | Hassovna | 436/69 |
| 5,120,537 | 6/1992 | Esmon et al. | 514/21 |
| 5,147,638 | 9/1992 | Esmon et al. | 514/12 |
| 5,279,956 | 1/1994 | Griffin et al. | 514/12 |
| 5,330,907 | 7/1994 | Philapitsch et al. | 435/23 |
| 5,426,097 | 6/1995 | Stern | 514/21 |
| 5,439,802 | 8/1995 | Rosen | 435/13 |
| 5,443,960 | 8/1995 | Dahlback | 435/13 |
| 5,453,373 | 9/1995 | Gerlitz et al. | 514/2 |

OTHER PUBLICATIONS

Faioni et al, "Blood"; vol. 71(4), pp. 940–946, (Apr. 1988).

*Primary Examiner*—Michael G. Wityshyn
*Assistant Examiner*—Louise N. Leary
*Attorney, Agent, or Firm*—Kalish & Gilster

[57] ABSTRACT

The present invention provides a novel one-stage assay which uses soluble thrombomodulin for directly determining the functional status in plasma of the vitamin K-dependent coagulation-inhibiting proteins, protein C and protein S. The method comprises combining a blood plasma test sample and a coagulation-activating substance in a calcium-free solution, then adding soluble thrombomodulin and calcium ions to initiate a coagulation reaction, measuring the time required for the test plasma sample to clot, comparing the measured clot time to that of standard control plasma samples, including protein C- and protein S-deficient plasma controls, and then using the compared clot time values for determining the functional status of protein C and protein S in the individual from whom the test plasma sample was taken. The functional status of the vitamin K-dependent coagulation-inhibiting proteins is used to determine the risk of thrombosis in the host individual.

15 Claims, 3 Drawing Sheets

SOLUBLE THROMBOMODULIN-BASED ONE-STAGE ASSAY FOR VITAMIN-K DEPENDENT COAGULATION-INHIBITING PROTEINS

This application is a continuation of application Ser. No. 07/771,644, filed Oct. 4, 1991, now abandoned.

FIELD OF THE INVENTION

The present invention relates to a novel one-stage blood coagulation assay which incorporates soluble thrombomodulin for the rapid and direct in vitro determination of the functional status of vitamin K-dependent coagulation-inhibiting proteins in a plasma sample. In particular, the functional status of protein C and protein S are reliably and sensitively determined with this assay, without separation from the plasma sample in which they are contained. In addition, the present invention relates to novel molecular complexes produced in the aforementioned one-stage blood coagulation assay.

BACKGROUND AND OBJECTS OF THE PRESENT INVENTION

The capacity of blood to clot and stop flowing from a wound is dependent on the proper functional interaction of a large number of factors and cofactors in the blood coagulation cascade. The ability of clinical laboratories to reliably and conveniently assay for these factors and cofactors in plasma samples from donor patients can be critical in monitoring individuals for whom either inappropriate coagulation episodes (such as occurs, for example, in disseminated intravascular coagulation disease) or inappropriate failure of blood to clot (such as occurs, for example, in hemophilia) is a daily life-threatening problem.

The physiologic basis for these clinically important coagulation problems can be exceedingly complex to diagnose. In most cases, however, diagnosis can be made by detecting either quantitative or functional changes in certain of the biological factors and cofactors which activate or regulate the coagulation process. A number of diagnostic assays have been developed which reliably measure many of the regulatory proteins involved in the coagulation cascade (see, for example, the textbooks by R. Hoffman et al., *Hematology: Basic Principles and Practice,* New York: Churchill Livingston Inc., 1991; and by C. Kjeldsberg et al., *Practical Diagnosis of Hematologic Disorders,* Chicago: American Society of Clinical Pathologists Press, 1989). These include such routine coagulation assays as the activated partial thromboplastin time (APTT) assay, the prothrombin time (PT) assay, and the thrombin clotting time (TCT) assay. In spite of extensive research, none of these assays directly measure, in a one-stage assay, the functional status in plasma of the vitamin K-dependent coagulation-inhibiting proteins, protein C and protein S. Because protein C and protein S are both essential in the normal regulatory process of down-regulating the blood coagulation cascade, the lack of any one-stage assay which directly determines both of their functional activities remains a serious deficiency in the art.

The need for a convenient one-stage assay for determining protein C and protein S function in plasma is emphasized by the fact that abnormalities in protein C and protein S function are more common in the population than is usually believed. For example, from 4-to-5% of the population as a whole have genetically-acquired protein C or protein S deficiencies, and a large number of these individuals have a clinical history of recurrent thrombotic (microvascular clotting) episodes (Gladson et al., *Thromb. Haemostas.* 59: 18, 1988). It is these individuals who should be regularly monitored for the functional activities of these coagulation-inhibiting proteins individuals who are known to be at high risk for recurrent thrombosis (which can be lethal) should be kept on lifelong maintenance anticoagulant therapy, with regular monitoring.

The coagulation enzyme system

To better appreciate the importance of such assays, and how activated protein C and protein S are involved in regulating the blood coagulation cascade, the following brief description of the coagulation enzyme system is provided.

The blood clotting system may best be viewed as a chain reaction involving the sequential activation of inactive enzyme precursors (zymogens) into active serine proteases. These activation events, which take place on the surfaces of cells such as platelets, white blood cells, and endothelial cells, have been divided into two distinct pathways termed the extrinsic and the intrinsic pathways of coagulation. A clot is generated in the intrinsic pathway by activation of those coagulation components which are all contained in (or are "intrinsic to") whole blood. In the extrinsic pathway, components intrinsic to whole blood are required along with an externally-supplied coagulation-activating substance known as "tissue factor" (also sometimes referred to as thromboplastin, thrombokinase, or blood coagulation factor III). Tissue factor is a cell surface protein extrinsic to blood, and is expressed by cellular injury. Whether a particular coagulation factor becomes activated in the extrinsic or the intrinsic pathway is important in selecting a particular coagulometric assay with which to detect and evaluate that particular factor.

Thrombin. The multistep coagulation chain reaction uitimately produces the enzyme thrombin, the last serine protease in the coagulation cascade, which, through limited proteolysis, converts fibrinogen molecules into an insoluble gel of fibrin fibers which forms the physical clot. Two key events in the coagulation cascade are the conversion of clotting factor X into an activated form, factor Xa, and the subsequent conversion of prothrombin by factor Xa into thrombin. Both of these conversion reactions occur on cell surfaces, such as, for example, the surfaces of platelets, and both reactions require cofactors. These cofactors, factors V and VIII, are in circulation in the form of relatively inactive precursor molecules. When the first few molecules of thrombin are formed, thrombin loops back and activates factors V and VIII through limited proteolysis. The activated factors, Va and VIIIa, accelerate both the conversion of prothrombin into thrombin and also the conversion of factor X to factor Xa, speeding the clotting process by approximately 100,000 fold. This significant amplification is essential in the timely formation of a clot. As will be discussed below, factors Va and VIIIa are the principal protein targets of activated protein C and protein S.

Thrombomodulin. Some of the thrombin formed during the formation of a clot is also bound by thrombomodulin, an essential reagent used in soluble form in the present invention. Thrombomodulin is a glycoprotein normally found fixed in the surface membranes of endothelial cells that form the lining of all blood vessels. While vascular endothelium once was thought to be a passive barrier which simply channeled the blood, it now is known that endothelial cells are actively involved in the regulation of intravascular coagulation mechanisms, and that much of this activity is due to the thrombomodulin in the endothelial cell membranes.

Thrombin-thrombomodulin complex. Thrombomodulin forms a tight, stoichiometric complex with thrombin, altering both the physical shape and functional properties of thrombin so that it no longer has procoagulant activity, i.e., it no longer converts fibrinogen to fibrin, activates platelets, or converts clotting factors V and VIII to their activated counterparts Va and VIIIa. Rather, the thrombin which is bound by thrombomodulin becomes an efficient activator of protein C. The rate constant for the activation of protein C by thrombin bound in a thrombomodulin-thrombin complex is about 20,000 fold higher than the rate constant for activation of protein C by thrombin found free in solution. Additionally, activation of protein C by thrombin in the absence of thrombomodulin is inhibited by calcium ions, whereas activation by the thrombin/thrombomodulin complex is a calcium-dependent reaction.

Thus, the coagulation-inhibiting effects of thrombomodulin are of two different types. One is a heparin-like anticoagulant effect in which the binding of thrombin to thrombomodulin inhibits the capacity of thrombin to enzymatically convert fibrinogen into fibrin fibers; the anticoagulant heparin exerts a similar antithrombin effect. This is the thrombomodulin-mediated anticoagulant effect most commonly observed by others (for example, see Gomi et al., Blood 75: 1396, 1990).

The second anticoagulant effect of thrombomodulin results from the activation of protein C by the thrombin-thrombomodulin complex. This effect is the key component of the present invention. When activated, protein C has the capacity to enzymatically cleave (via hydrolysis) both factor Va and factor VIIIa, substantially inhibiting both of their clot-promoting activities. In the presence of its vitamin K-dependent cofactor protein S, the rate of activated protein C-mediated hydrolysis of factors Va and VIIIa is increased by about 25 fold compared to hydrolysis in the absence of protein S. Thus, one of the important mechanisms operating in the vascular endothelium to maintain the normal anticoagulant state of the endothelial surface is the pathway by which a thrombin-thrombomodulin complex activates protein C to form a coagulation-inhibiting activated protein C-protein S complex on a cell surface.

The vitamin K-dependency of the protein C and protein S coagulation-inhibiting proteins derives from the fact that a vitamin K-dependent microsomal carboxylase enzyme in the liver forms an unusual amino acid, gammacarboxyglutamic acid, in a post-ribosomal carboxylation step in the precursor proteins of both protein C and protein S. The appearance of the gammacarboxyglutamic acid moieties in these protein molecules is crucial in that it facilitates their efficient binding via a calcium-mediated bridge, to phospholipid-containing surfaces such as, for example, the surfaces of platelets, endothelial cells, and, importantly for in vitro coagulometric assays, phospholipid micelles in solution. As noted below, the binding of the carboxylated glycoproteins to a phospholipid surface allows the proteins to concentrate, interface and interact with one another more efficiently in three-dimensional space. Several in vitro clotting assays take advantage of this fact, in that phospholipids are included among the necessary reagents used in the coagulometric assays.

Phospholipid. All clotting reactions with meaningful rates are viewed as occurring on a surface. Crucial to the efficient interaction of thrombomodulin (the cofactor), thrombin (the enzyme), and protein C (the substrate) is the presence of calcium ions and an integrating surface such as is found, for example, on a soluble phospholipid micelle (a submicroscopic phospholipid sphere). On such a surfacer the three reactants are brought into close proximity, thereby substantially increasing their effective concentrations and their reaction rate many fold. It is believed that all relevant soluble complexes which contain soluble thrombomodulin, thrombin and activated protein C, and which produce vitamin K-dependent anticoagulant activity, also contain an essential surface component. The in vitro clotting assays of the present invention take advantage of this fact by the use of a suitable phospholipid (cephalin) in a preferred embodiment.

Protein C and Protein S assays

Until the present invention, it has not been possible to conveniently measure the functional activities of both protein C and protein S in a simple and rapid one-stage in vitro assay. This is because soluble thrombomodulin has never before been added directly into laboratory coagulometric assays to detect protein C zymogen. Rather, thrombomodulin has been added with thrombin as a preactivation reagent, either as a soluble complex, or in an immobilized form and in conjunction with a process which required either prior separation of protein C from other plasma components or the subsequent removal of activated protein C from other plasma components in order to carry out the final determination of activated protein C in a separate coagulometric or amidolytic assay. Thus, the anticoagulatory effect of soluble thrombomodulin, in the form of soluble thrombomodulin-thrombin complexes, has never been exploited directly in conventional clinical assays.

Protein C assays

For protein C, a number of different assays are available for its determination (as reviewed in detail by Löbermann et al., *Behring Inst. Mitt.* 79:112, 1986; Vigano-D'Angelo et al., in *Biotechnology in Clinical Medicine* [Albertini et al., editors] New York: Raven Press, 1989: and more recently by Preissner, *Clin. Sci.* 78: 351, 1990). The assays generally fall into three categories: antigenic detection assays, chromogenic (amidolytic) assays, and functional coagulometric assays.

Protein C antigenic assays. For determination of protein C antigen concentration in plasma, detection assays include electroimmunoassay, radioimmunoassay, and ELISA-type assays. Not only polyclonal antibodies from rabbit or goat, but also monoclonal antibodies have been used as detecting reagents in these assays. While in vitro detection of protein C with antibodies is a sensitive procedure, antigenic detection provides little or no information regarding the functional capacity of the protein C detected.

Protein C chromogenic assays. Alternatively, because activated protein C is an enzyme, its presence in a plasma sample can be quantified with a chromogenic substrate. Prior activation of protein C, with exposure of the enzymatic active site, is required for expression of its enzymatic activity. However, the relatively small size of the synthetic chromogenic substrate (about 600 daltons) commonly used in these assays may permit satisfactory proteolysis of the synthetic substrate, while missing defects in the functional integrity of protein C which would prevent proteolytic cleavage of factor Va and VIIIa, the biological substrates of activated protein C which each have molecular weights of about 300,000 daltons. Moreover, the interaction of activated protein C with its cofactors (protein S, calcium ions, and phospholipid), which requires that all functional features of the protein C molecule be intact, is not evaluated by chromogenic assays. It is important to be aware of this, since protein C molecules detected in chromogenic assays can still be deficient in functional anticoagulant capacity.

Protein C coagulometric assays. For determination of functional capacity of protein C molecules in a plasma sample, coagulometric assays offer the advantage of evaluating the coagulation-inhibiting activity of activated protein C in the presence of its usual biological substrates and cofactors, thereby reflecting more accurately the physiologic state of the protein C in the particular plasma sample being evaluated.

The protein C in a plasma sample is commonly activated before it is assayed. This activation is done either with or without prior separation of protein C from other plasma components. Isolation of the protein C from the test plasma sample has (up until the present invention) been necessary if the protein C is to be activated by thrombin or by the physiological activator, which is the thrombin/thrombomodulin complex. Unfortunately, because of poor reaction kinetics, activation of protein C with thrombin in the absence of thrombomodulin does not lead to complete activation of protein C in the sample. In contrast, when thrombin is bound to thrombomodulin, the rate of activation is increased by about 20,000 fold over the rate obtained with thrombin alone.

Activation can also be carried out without prior isolation of protein C from the test plasma sample by use of a snake venom activator such as, for example, southern copperhead venom, or the "PROTAC® C" reagent (the latter from Pentapharm, Basel, Switzerland).

After either of the above procedures, the anticoagulant activity of activated protein C is assessed most commonly either by prolongation of the otherwise routine activated partial thromboplastin time (APTT) assay, or in a factor Xa one-stage coagulometric assay. The clot time in this latter assay is a function of the conversion of prothrombin to thrombin, and is initiated by the addition of exogenous factor Xa to the plasma sample in the presence of calcium ions and a phospholipid component. The assay is sensitive to activated factor V, but not to activated factor VIII. In this system, addition of preactivated protein C from the test plasma sample to a control plasma sample prior to the addition of factor Xa prolongs the clot time as a result of its ability to inactivate factor Va generated during the reaction.

In stark contrast to the commonly used assays discussed above, the novel assay of the present invention does not require preliminary isolation of protein C from a plasma test sample; it permits the activation of protein C with its physiological activator, the thrombin/thrombomodulin complex; and it results in a determination of protein C functional activity in the test sample, all in a simple one-stage procedure.

Protein S assays

Laboratory evaluation of protein S status is complicated by the fact that two forms of protein S are present in plasma. In plasma, about 40% to 50% of the protein S is free and serves as the cofactor for activated protein C. The remaining 50% to 60% of plasma protein S is complexed to C4b binding protein ("C4bBP") and, as such, is unavailable as an anticoagulant. That C4bBP is an acute phase protein and is elevated during inflammation further complicates evaluation of protein S status. This rise in C4bBP favors a transient shift of the protein S to the complexed form, thereby inducing a relative and transient protein S deficiency state. Because protein S which is bound to C4bBP in plasma is no longer able to function as a cofactor with activated protein C, individuals with serious inflammatory disorders are often at risk for thrombosis. This is an acquired situation which will rise and fall, and even disappear, depending on the state of the inflammatory disorder.

In the clinical laboratory, a very limited number of tests are available to assess protein S status, and these are generally antigen detection assays. These tests include polyethylene glycol precipitation of bound protein S with subsequent measurement of the free protein S remaining in the plasma; crossed immunoelectrophoresis for protein S, which separates free and bound forms of protein S but is not quantitative; and enzyme-linked immunosorbent assays (ELISA). ELISA assays are suitable in combination with PEG precipitation to quantitate free protein S. However, while ELISA assays may detect protein S with sensitivity, such antigen detecting assays provide little or no information regarding the functional capacity of the protein S detected. Unfortunately, standardized functional assays for protein S are not yet available in the general clinical laboratory.

It is, therefore, a principal object of the present invention to provide a convenient and reliable one-stage assay by which both of the vitamin K-dependent coagulation-inhibiting proteins, protein C and protein S, can be quantitatively and functionally determined in a blood plasma test sample in a clinical laboratory.

It is another object of the present invention to provide a soluble coagulation-inhibiting complex comprising soluble thrombomodulin, thrombin and protein C, bound to a soluble phospholipid surface. Such a phospholipid surface is found, for example, on soluble phospholipid micelles.

It is still another object of the present invention to provide a soluble complex comprising activated protein C and its cofactor, protein S, bound to a soluble phospholipid surface.

Yet another object is to provide a soluble complex comprising activated protein C, protein S and factor Va bound to a soluble phospholipid surface.

Still another object is to provide a soluble complex comprising activated protein C, protein S and factor VIIIa bound to a soluble phospholipid surface.

SUMMARY OF THE PRESENT INVENTION

In accordance with the present invention, there is provided a novel one-stage assay which uses soluble thrombomodulin for determining in a novel blood coagulation assay the functional status of vitamin K-dependent coagulation-inhibiting proteins in plasma. The method comprises combining a blood plasma sample and a coagulation-activating substance in a calcium-free solution, then adding soluble thrombomodulin and calcium ions in amounts sufficient to initiate a coagulation reaction, measuring the time required for the plasma test sample to clot, comparing the measured clot time to that of standard control plasma samples, and then using the compared clot time values for determining the risk of thrombosis in the individual from whom the plasma test sample was taken.

In a preferred embodiment of the present invention, soluble thrombomodulin is added simultaneously with the calcium ions (i.e., the recalcification step), and the subsequent extension of the clot time caused by the anticoagulant effect of the soluble thrombomodulin is compared to the extension of clot time that is observed in protein C- and/or protein S-deficient plasma samples used as deficient plasma controls.

The vitamin K-dependent coagulation inhibiting factors with which the present invention is principally concerned are protein C and protein S, both of which are essential regulatory factors in maintaining the anticoagulatory state of the endothelial cell lining of all blood vessels in the body. Any other coagulation-inhibiting protein, the functional status of which may be determined in these assays by using the methods taught herein, are also included within the scope of the present invention.

The coagulation-activating substance added to the mix of reagents at the beginning of the assay of this invention is, in the preferred embodiment, the "DADE®/ACTIN® ACTIVATED CEPHALOPLASTIN REAGENT". This reagent is available commercially from the Baxter Healthcare Corporation and is more fully described in its package insert No. L10293-BH-H (revised 10/88) (Baxter/Dade, Miami, Fla.), the content of which is incorporated herein by reference. The coagulation-activating ingredient in this reagent is ellagic acid, a negatively-charged organic compound of formula $C_{14}H_6O_8$, having a molecular weight of about 302 daltons.

In another embodiment, the coagulation-activating substance is factor Xa. Factor Xa acts upon prothrombin in the presence of factor V, calcium ions and phospholipid to form a complex which activates prothrombin, converting it to thrombin.

In another embodiment, the coagulation-activating substance is a reptilase, preferably, Russell's viper venom, which is available from a variety of commercial sources. Russell's viper venom is an activator of factor X, enzymatically cleaving factor X to generate factor Xa, which is the procoagulant factor just discussed.

In yet another embodiment, the coagulation activating substance is a protein known as "tissue factor", which is a cell surface protein released into blood following cellular damage. Tissue factor is a membrane receptor for factor VII, and is available from a variety of commercial sources. In conjunction with tissue factor and calcium ions, factor VII enzymatically modifies factor X, converting factor X to its procoagulant form, factor Xa, discussed above.

In still other embodiments, coagulation activating substances include negatively-charged collagen molecules; or negatively-charged foreign surfaces such as micronized silica, kaolin, fine glass or metal beads, and even wooden applicator sticks. The use of these latter particulates are limited, however, to assays in which the presence of such insoluble foreign surfaces will not interfere in carrying out the assay.

In the preferred embodiment of the present invention, the phospholipid added to the assay is cephalin, a glycerophosphoric acid extracted from dehydrated rabbit brain, and contained as an active ingredient in the "DADE®/ACTIN® ACTIVATED CEPHALOPLASTIN REAGENT", as more fully described in the Baxter Healthcare Corporation package insert No. L10293-BH-H [revised 10/88] (Baxter/Dade, Miami, Fla.). Biochemically, cephalins consist of glycerophosphoric acid in which the two free hydroxyls of the molecule are esterified with long-chain fatty acid residues, and ethanolamine forms an ester linkage with the phosphate group. All natural cephalin products occur in alpha-forms, which have the following generic structure:

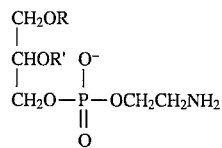

where R and R' can be, but are not necessarily, identical fatty acids.

Other phospholipids which may be used in further embodiments of the present invention are those which successfully facilitate the activation of protein C and its detection in the coagulometric assays of the present invention. It is believed that all relevant soluble complexes which contain soluble thrombomodulin, thrombin and activated protein C, and which produce vitamin K-dependent anticoagulant activity, also contain an essential surface component. The in vitro clotting assays of the present invention take advantage of this fact by the use of a suitable phospholipid (cephalin) in a preferred embodiment. However, besides phospholipids, any micelle-forming (or liposome-forming) ingredient which is amphipathic and whose charge distribution and size make it optimal for use as a surface carrier in facilitating the coagulometric assays disclosed in the present invention is included within the scope of the coagulation-activating agents of the present invention.

By the term "normal control plasma" as used above and hereinafter is meant a plasma sample which contains the usual (statistically common) and expected amounts of all known coagulation-related factors which are essential in promoting the clotting of plasma by either the intrinsic or the extrinsic coagulation pathways. Such factors are known to those skilled in the art, and usual (statistically common) values, with normal range of values, are to be found in such well-known textbooks as that by C. Kjeldsberg et al., *Practical Diagnosis of Hematologic Disorders,* Chicago: American Society of Clinical Pathologists Press, 1989. It is also standard practice in the art to combine plasma samples from a large number of normal, healthy volunteer donors to generate a larger "pooled" batch of normal plasma. The advantage of such a pool is that normal plasma samples with identical control values will be available over a long period of time, especially if such standardized control samples are preserved in a frozen or lyophilized (freeze-dried) state.

The term "test sample" or "plasma test sample" as used above and hereinafter simply refers to a plasma sample in which the protein C or protein S content are not yet known, and which is the subject of the coagulometric assay.

It is to be understood that any of the preferred assays of the present invention, when properly set up, can be used to detect the presence or the functional activity of the coagulation-inhibiting proteins, protein C and protein S in a plasma sample; i.e., they can be used to detect or to measure protein C and/or protein S qualitatively or quantitatively, respectively. Thus, the terms "detect" and "detecting", "measure" and "measuring", and "determine" and "determining" as used above and hereinafter are meant to cover both the quantitative and the qualitative aspects of the assays.

In accordance with the present invention, there are also provided several molecular complexes which are novel compositions of matter produced by the process of the assay itself.

DETAILED DESCRIPTION OF THE PRESENT INVENTION

Figure 1:
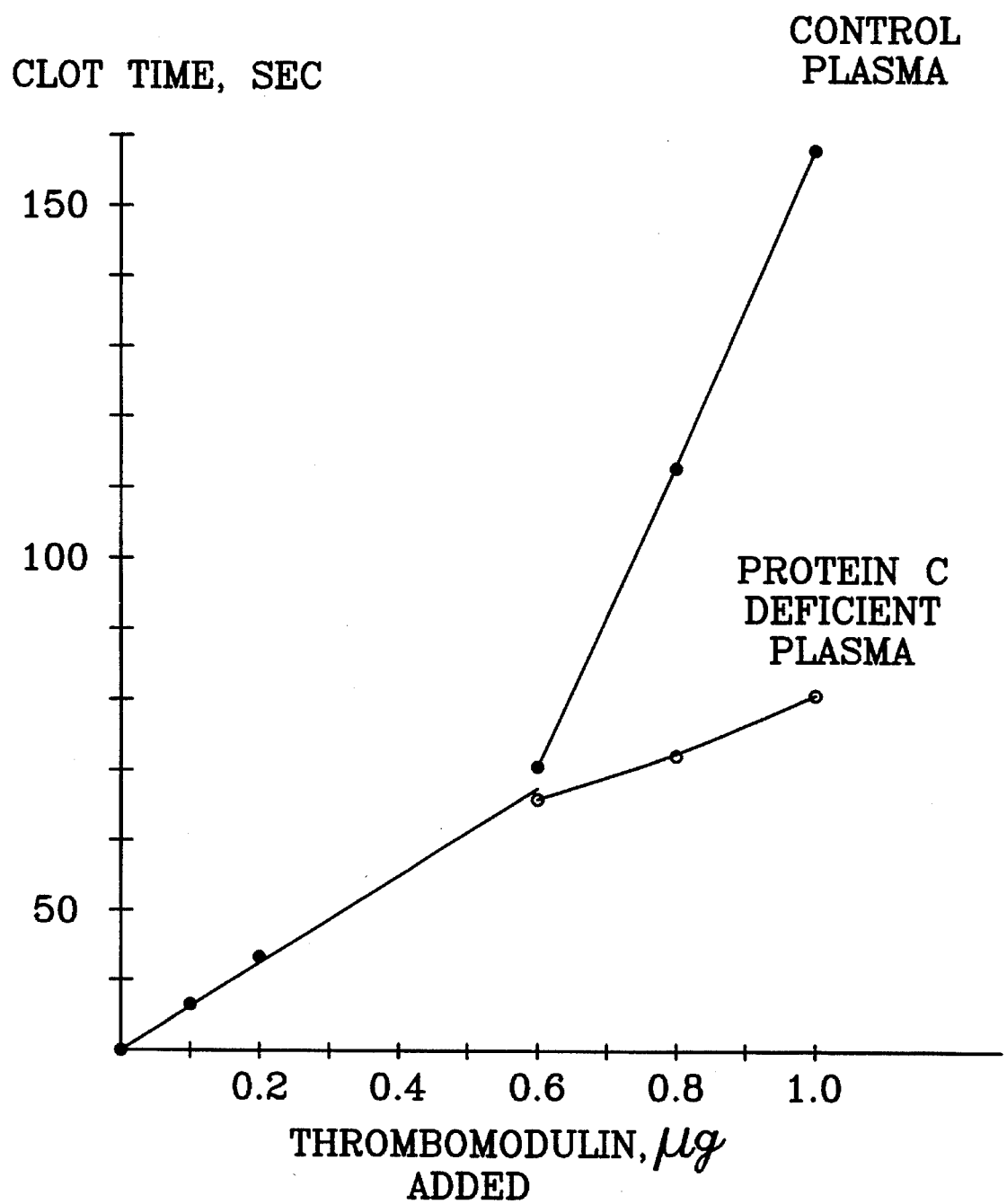
FIG. 1 is a line graph which demonstrates that inclusion of soluble thrombomodulin in a coagulometric assay has a significantly different anticoagulant effect on a protein C-deficient plasma sample than it does on a normal control plasma sample. The final amount of soluble thrombomodulin (in micrograms) added to the assay is plotted versus clot time (in seconds) for each sample mixture. The curve with filled circles (●) represents the normal control plasmas and the open circles (○) represent the protein C-deficient plasma.

Novel one-stage coagulometric assay of the present invention.

The following is a detailed description of the novel assay of the present invention useful for directly determining in a plasma sample the functional activities of the vitamin K-dependent coagulation-inhibiting proteins, protein S and protein C. Also provided are descriptions of the necessary reagents and instrumentation used in a preferred embodiment of the present invention. The invention takes advantage of the kinetic environment of an in vitro coagulometric assay to detect the thrombin-mediated coagulation-inhibiting activity of protein C and protein S, and does so, in a preferred embodiment, in an assay in which all of the clotting factors of the intrinsic (in contradistinction to the extrinsic) coagulation pathway are involved, including clotting factors V and Va, and VIII and VIIIa.

Plasma specimen collection and preparation. In preparing plasma specimens for analysis in the coagulometric assay of the present invention, nine parts of freshly-collected patient blood are mixed thoroughly with one part of 3.8% sodium citrate anticoagulant. The anticoagulated blood specimen is then centrifuged for a minimum of 10 minutes at 1000×G to pellet the large cellular components of the blood. The supernatant plasma is removed to a plastic tube, stoppered, and refrigerated at 4°–6° C. until used. Patient plasma is tested within two hours of blood collection to ensure validity and reproducibility of results, and is never held at 37° C. for more than five minutes. Human plasma prepared in a similar manner can also be obtained from American Red Cross blood centers.

Coagulation-activating substance. In performing the coagulometric assay of the present invention, the preferred reagent for use in initiating coagulation in the assay cup is the "DADE®/ACTIN® ACTIVATED CEPHALOPLASTIN REAGENT", commercially supplied by Baxter Healthcare Corporation (Miami, Fla.), and described in the Baxter Healthcare Corporation package insert No. L10293-BH-H (revised 10/88). The active ingredients in this commercial reagent are the negatively-charged organic compound, ellagic acid, and the phospholipid, cephalin, extracted from dehydrated rabbit brain. Use of soybean phospholipid (lecithin) in place of cephalin did not give commercially adaptable results.

Other Reagents used in the one-stage coagulometric assay.

The following reagents are also required for use in the one-stage coagulometric assay of the present invention:

1) saline, prepared as a 0.9% sodium chloride solution in water;

2) soluble thrombomodulin, isolated from rabbit lung tissue and purified according to the procedures of Esmon & Owen (*Proc. Natl. Acad. Sci. USA* 78: 2249, 1981), and prepared in buffered saline at a final concentration appropriate to the assay; and 3) calcium chloride, prepared as a 25 millimolar solution in water.

The crucial feature of the assay of this invention is the use of soluble thrombomodulin as an additive to the coagulation reaction mixture. The use of soluble thrombomodulin for the activation of protein C in an in vitro coagulometric assay is believed to be unique. When added to the other reagents in the reaction mixture, soluble thrombomodulin provides a highly reactive substrate for the subsequent high-affinity binding of free thrombin. In the presence of calcium, the thrombin in the thrombin-thrombomodulin complex then activates protein C, which, together with protein S, degrades the clot-promoting factors Va and VIIIa in the plasma. Thus, using soluble thrombomodulin anticoagulant as one of the assay reagents, and using protein C-and protein S-deficient plasma samples as deficient plasma controls, the coagulation-inhibiting activities of protein C and protein S can be directly determined in a novel one-stage assay procedure.

As noted above, the coagulometric assay of this invention for protein C and/or protein S is a one-stage assay because the assay is characterized by a single incubation. In contrast the prior art assays for protein C activate protein C during a prior preactivation step, followed by an incubation to detect the activated protein C formed, and, thus, constitute two-stage assays. Exemplary is the use of copperhead snake venom or "PROTAC-C", discussed above.

In one embodiment of this invention, the active ingredients and other reagents and controls of this invention constitute the components of a commercial assay kit for determining the functional status of vitamin K-dependent coagulation-inhibiting proteins, namely, protein C and protein S. For example, in addition to the soluble thrombomodulin and the coagulation-activating agent of this invention, such a kit optionally contains one or more components selected from (i) a positive control, e.g., a normal plasma sample, (ii) a negative control, e.g., protein C and/or protein S deficient plasma samples, and (iii) a buffered solution containing a calcium salt, e.g., calcium chloride.

Instrumentation used. In a preferred embodiment of the present invention, a Fibrometer™ coagulation timer (Becton, Dickinson and Company Rutherford, N.J.) is used to determine the clot time in the coagulometric assay. When the Fibrometer™ is used, the probes must be thoroughly washed with distilled water and wiped dry with lint-free tissue between tests to prevent carryover of activated plasma proteins. Since there are two different types of probes available for this instrument, a 0.3-ml probe and a 0.4-ml probe, it is necessary to design the assay so that the final volume of reagents added to the reaction cups matches the requirements of the probe which is used.

Coagulation controls. With each series of tests, standard clot time curves are prepared using several control plasma samples in order to ensure the quality, reproducibility and interpretability of the data obtained. The control plasma samples are run in the same manner as the test samples, and establish a range of allowable variation for the control clot time values.

In the present invention, protein C-deficient and protein S-deficient plasma samples, used as factor-deficient plasma controls, were prepared by immunoabsorption of different batches of the same citrated human plasma. Immunoabsorption was carried out using immobilized polyclonal antibodies. For example, to prepare protein C-deficient plasma, one volume of the citrated plasma was mixed in a batch preparation immunoabsorption procedure with nine volumes of anti-protein C coupled to Sepharose®. In contrast, to prepare protein S-deficient plasma, plasma was passed over a polyclonal antibody-Sepharose® affinity column, in a chromatography process well known in the art. Regardless of the immunoabsorption method used, however, it must be noted that the concentration of factors V and VIII may be altered during the processing. Since these factors are crucial in the clotting cascade and are the principal protein targets of activated protein C and protein S as described earlier, alterations in their concentrations will affect the coagulability of and the outcome of assays using the processed plasma samples. Accordingly, the concentrations of factors V and VIII in processed plasma samples must be standardized following immuno-absorption.

Assay Results. The results obtained in the coagulometric assays of the present invention are reported in seconds, and are related to a "normal range" of clot time values obtained in each laboratory. This normal range is established by obtaining plasma samples from a large number of normal healthy donors (for example, from 25 to 40 individuals), and determining the range of statistically common clot time values for these normal donors when tested in the same laboratory. The number of donors needed to establish a statistically acceptable range is determined by each laboratory. Blood is collected by the same method used for collecting test samples from patients, and clot times, using the assay of the present invention, are determined on each normal citrated plasma.

In like manner, a range of values common to populations other than normal, healthy adults is also established as warranted. For example, it may be of interest to establish normal ranges in selected age groups such as pediatric groups or the elderly; or in certain risk groups such as smokers, alcoholics, or individuals on certain medications.

The following examples demonstrate methods and describe protocols useful in practicing the present invention.

EXAMPLE 1

A one-stage functional assay of protein C in normal plasma.

In these studies, a Becton-Dickinson Fibrometer® with a 0.4-ml probe was used. The following reagents were placed into a coagulation cup, with care to add them quickly but accurately:

a) 0.1 ml of the "DADE®/ACTIN® ACTIVATED CEPHALOPLASTIN REAGENT" ( as described hereinabove);

b) 0.1 ml of normal plasma or protein C-deficient plasma. As soon as these reagents were added into the cup, a timer was started, the reagents were mixed well, and incubated at 37° C. for exactly 90 seconds. During this brief incubation time, the calcium-independent preactivation of the intrinsic coagulation cascade begins, with the activation of factor XII by kallikrein on negatively charged surfaces, forming factor XIIa, an enzyme which catalyzes the conversion of factor XI, a proenzyme, to its active enzyme form, factor XIa. The rapid preactivation process stops here, in the absence of added calcium ions. At 90 seconds, the following were then added:

c) from 1 to 10 microliters of soluble thrombomodulin (equivalent to 0.1 to 1 micrograms of soluble thrombomodulin, respectively);

d) sufficient volume of prewarmed (37° C.) saline to bring the volume to 0.1 ml;

e) 0.1 ml of prewarmed 25mM $CaCl_2$.

The total volume in the coagulation cup was 400 microliters. Precisely as the calcium chloride was added, the Fibrometer™ timer and probes started automatically. The elapsed time until detection of a fibrin clot was determined automatically by the instrument. The indicated clot time was recorded for each assay cup in a replicate group.

The amount of soluble thrombomodulin added to the coagulometric assay was important. As shown in TABLE 1, the anticoagulant effect of soluble thrombomodulin in the presence of normal control plasma increased in direct proportion to the amount of thrombomodulin added to the assay, The control assay cup which contained only dialyzing buffer, and which lacked thrombomodulin, clotted in 30.4 seconds, whereas the addition of 1 microgram of soluble thrombomodulin increased this clot time more than five fold.

TABLE 1

| Clot time (seconds) in coagulometric assay containing different amounts of soluble thrombomodulin. | | |
|---|---|---|
| Thrombomodulin | Clot time (seconds) | |
| (micrograms) | Control Plasma | [a]Deficient Plasma |
| 0.1 | 37.9 | |
| 0.2 | 43.9 | |
| 0.6 | 69.8 | 64.8 |
| 0.8 | 112.9 | 71.8 |
| 1.0 | 156.9 | 81.3 |
| buffer only | 30.4 | |

[a]Plasma was deficient in protein C

These data also demonstrate that soluble thrombomodulin had a significantly different anticoagulant effect on protein C-deficient plasma than it did on normal control plasma. When these same data were plotted as amount of soluble thrombomodulin added (in micrograms) versus clot time (in seconds), two very different clot time lines were obtained, as shown in FIG. 1.

It is important at this point to realize that the principal difference between the two plasma samples in this test was the presence of functional protein C molecules in the normal plasma sample compared to the absence of these molecules in the protein C-deficient plasma sample. Thus, the difference in slope of the two lines in FIG. 1 reflects primarily the presence or absence of this coagulation-inhibiting protein.

Since soluble thrombomodulin exerts dual anticoagulant functions (one being its heparin-like effect which prevents thrombin from converting fibrinogen into fibrin; and the other being its role in converting protein C into activated protein C, which then degrades factors Va and VIIIa in the coagulation cascade), the clot time curve associated with the protein C-deficient plasma is a reflection solely of the heparin-like activity of thrombomodulin. In contrast, the clot time curve of the normal plasma is a reflection of the combination of the heparin-like activity of thrombomodulin and its protein C activating capacity. Hence, the difference in the clot times between the two curves in FIG. 1 is a novel and simple way to demonstrate and quantify the functional presence of protein C in the normal plasma sample.

EXAMPLE 2

Sensitivity of the one-stage coagulometric assay for determining protein S and protein C functional deficiencies in plasma.

A one-stage functional assay of both protein C and protein S was set up essentially the same as in EXAMPLE 1, except that a) a constant amount (1 microgram) of soluble thrombomodulin was added to each assay cup; and b) the normal and deficient plasma samples were mixed together in varying proportions, in a final volume of 100 microliters, to create a series of plasma test samples with different levels of protein C or protein S, from 100% down to 0% of normal. The normal control plasma had full protein C and protein S activity.

Figure 2:
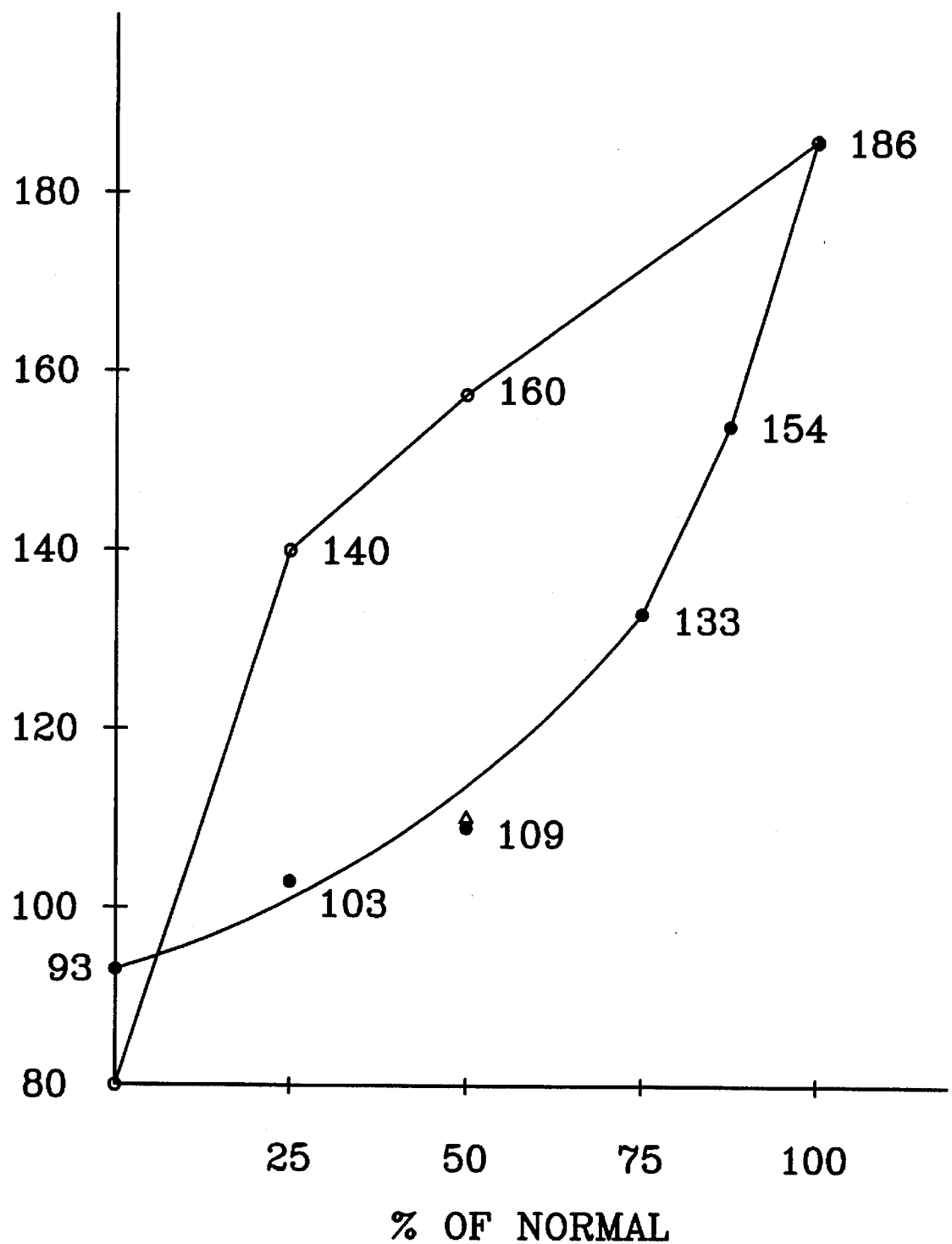
FIG. 2 shows the results of coagulometric assays in which protein S and protein C functional activity are determined using the same methodological embodiment of the present invention. The concentration of normal plasma used to dilute each of the protein C- and protein S-deficient plasma samples is plotted versus clot time (in seconds) for each sample mixture. In this series of studies, an identical amount (about one microgram) of soluble thrombomodulin was added to each assay cup. The filled circles (●) identify the protein C curve, and the open circles (○) identify the protein S curve. The point identified by the open triangle (△) marks the clot time of a mixture of 50% S-deficient and 50% C-deficient plasma.

The results from these experiments are shown in FIG. 2, in which the filled circles (●) identify the protein C curve, and the open circles (○) identify the protein S curve. The point identified by the open triangle (△) marks the clot time of a mixture of 50% S-deficient and 50% C-deficient plasma.

The clot time curves for the protein C- and protein S-deficient plasma types were substantially different, as shown. Bearing in mind that the part of an assay dilution curve wherein the assay is most sensitive to a change in the concentration of the measured protein is the region comprising the steepest part of the curve, it is clear that the relative dilutions of protein C- or protein S-deficient plasma at which the coagulometric assays are most sensitive for those factors are substantially different. As shown in FIG. 2, the clot time curve using protein C-deficient plasma is steeper (and therefore more sensitive) in the range of 50% or greater normal plasma than it is in the range of 0 to 50% normal plasma. In contrast, the protein S clotting curve is much steeper (and therefore more sensitive) in the range of from 0 to 25% normal plasma.

These data indicate that:

a) assays to detect protein S functional deficiencies can be satisfactorily performed using dilute preparations of the patient plasma test sample (i.e., small volumes of test plasma relative to the volume of protein-S deficient plasma); and that b) under the same reaction conditions (i.e., about 1 microgram of thrombomodulin in the assay), assays for the sensitive, detection of protein C functional deficiencies can be performed using small volumes of protein C test plasma mixed into a normal control plasma.

In a more practical application of the present invention, these data also indicate that, under the same react on conditions outlined above (i.e., approximately 1 microgram of thrombomodulin in the assay), assays to detect protein C functional deficiencies permit significantly smaller amounts of protein C-deficient plasma to be mixed into the test plasma sample (i.e. cannot be carried out satisfactorily on dilute preparations of the patient plasma test sample if the diluent is protein C-deficient plasma). Under these conditions, protein C in small amounts of test plasma may be satisfactorily measured by admixture with normal control plasma, thus taking advantage of the sensitive range of protein C detection shown in FIG. 2.

In an effort to improve the sensitivity with which protein S functional deficiencies could be detected, the amount of soluble thrombomodulin in the coagulometric assay of the present invention was raised from 1 microgram (as used above in EXAMPLE 2) to 2 micrograms, as shown in the following example.

EXAMPLE 3

Figure 3:
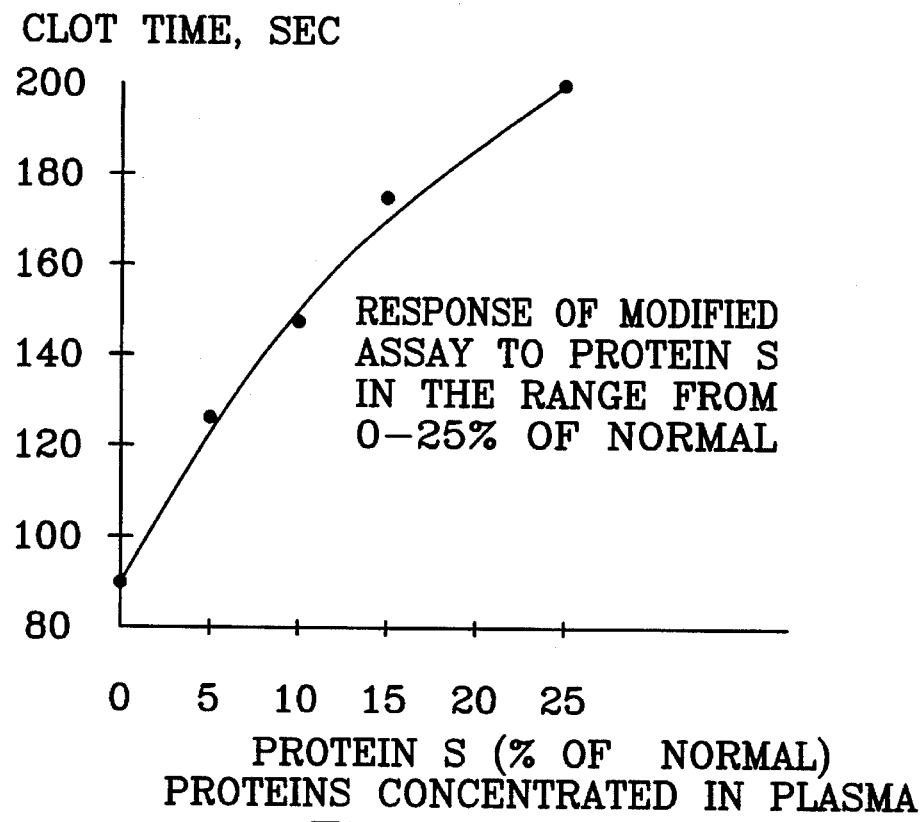
FIG. 3 shows the results of a coagulometric assay in which protein S functional activity was determined in a normal plasma sample. The concentration of normal plasma added to a protein S-deficient plasma sample is plotted versus clot time (in seconds) for each sample mixture. In contrast to the data in FIG. 2, the amount of thrombomodulin used in these assays was about 2 micrograms (instead of about 1 microgram) to determine if higher thrombomodulin levels would make the protein S functional assay more sensitive, and therefore more useful, for determining protein S functional activity.

Use of higher concentrations of soluble thrombomodulin to determine protein S function Doubling (to 2 micrograms) the amount of soluble thrombomodulin reagent added to the coagulometric assay made the assay more sensitive to determining protein S functional activity. As shown in FIG. 3, a substantial range of clot times (from approximately 90 seconds to 200 seconds; a range of about 110 seconds) was observed when protein S was assayed at concentrations varying from 0% (equivalent to 100% protein S-deficient plasma) to 25% of normal (equivalent to 3 parts protein S-deficient plasma to 1 part normal plasma). Thus, by adding about 2 micrograms of soluble thrombomodulin to the assay system, the assay became substantially more sensitive to protein S in the test samples than was detected using only 1 microgram of soluble thrombomodulin. Therefore, the sensitivity with which protein S functional deficiencies in plasma are detected is dependent on the concentration of thrombomodulin used in the assay.

It was important to compare these results with those of an assay for protein S based on adding exogenous, preactivated protein C into a coagulometric assay. The following example demonstrates that, in the absence of soluble thrombomodulin, the results were substantially different and were not as useful as the results obtained from assays which incorporated soluble thrombomodulin.

EXAMPLE 4

Figure 4:
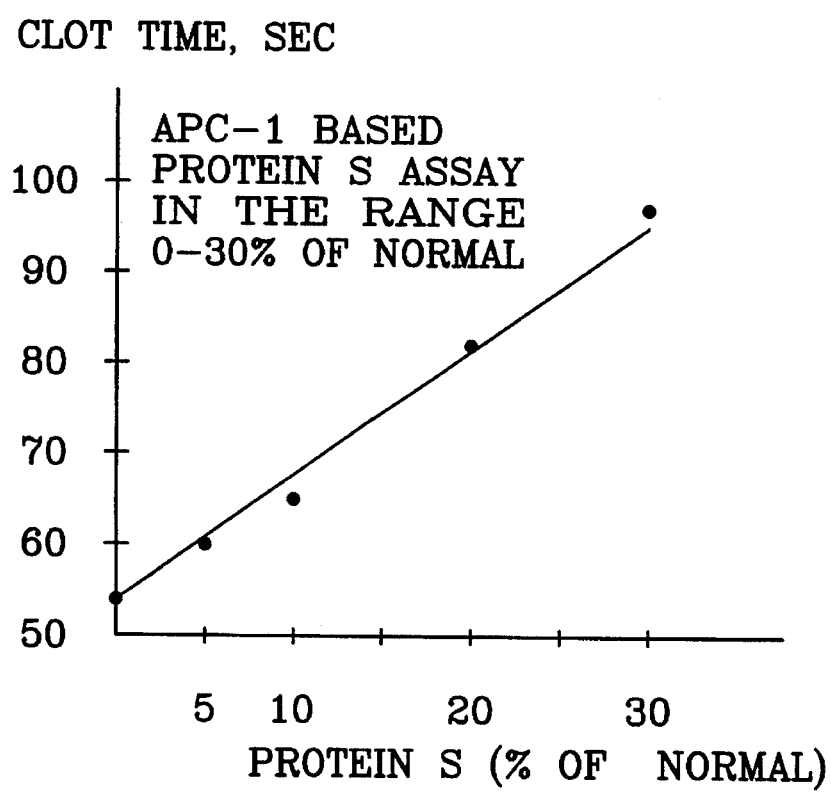
FIG. 4 shows the data from a coagulometric assay in which protein S functional activity was determined in a normal plasma sample to which pure in vitro-activated protein C, but not soluble thrombomodulin, was added at the beginning of the assay. The concentration of normal plasma added to a protein S-deficient plasma sample is plotted versus clot time (in seconds) for each sample mixture.

Adding activated protein C instead of soluble thrombomodulin to a coagulometric assay for protein S The data in FIG. 4 were obtained in an assay which utilized activated protein C, but not soluble thrombomodulin, as a coagulation-inhibiting protein factor. In a Fibrometer™ coagulation cup, the following were added:

a) 0.1 ml of "DADE®/ACTIN® ACTIVATED CEPHALOPLASTIN REAGENT" described in detail above;

b) 0.1 ml of plasma; and c) 0.4 micrograms of activated protein C.

These reagents were incubated at 37° C. for exactly 90 seconds, at which time 0.1 ml of saline was added, followed immediately by 0.1 ml of calcium chloride, activating the clotting reaction and the instrument timer.

The data show that the range in clot time (from approximately 54 seconds with undiluted protein S-deficient plasma, to about 89 seconds with 75% protein S-deficient plasma; a range of only about 35 seconds) was approximately one-third of the range in clot time shown in FIG. 3 in the previous example. Because the change in reagents reduced the range of assay responses by nearly 67%, it is clear that adding activated protein C instead of soluble thrombomodulin into the coagulometric assay did not provide as useful a measure of protein S function as was found in the coagulometric assay of the previous examples.

It will be appreciated that changes may be made in the nature, composition, operation and arrangement of the various elements, steps and procedures described herein without departing from the spirit and scope of the invention as defined in the following claims.

What is claimed is:

1. A one-stage blood coagulation method for directly determining the activity of a vitamin K-dependent coagulation-inhibiting protein selected from the group consisting of protein C and protein S in plasma, said method comprising combining a blood plasma test sample and a coagulation-activating substance in a calcium-free solution, then adding soluble thrombomodulin and calcium ions to the resultant mixture to initiate a coagulation reaction, measuring the time required for said test plasma sample to clot, comparing the measured clot time to that of standard control plasma samples, and then using the compared clot time values for determining the activity of protein C and protein S in the individual from whom said plasma test sample was taken.

2. The method of claim 1 wherein said vitamin K-dependent coagulation-inhibiting protein is protein S.

3. The method of claim 1 wherein said blood plasma test sample is obtained from a human donor.

4. The method of claim 3 wherein said human donor is a clinical subject.

5. The method of claim 1 wherein said coagulation-activating substance is a negatively charged organic molecule.

6. The method of claim 5 wherein said negatively charged molecule is ellagic acid.

7. The method of claim 1 wherein said coagulation-activating substance is tissue factor.

8. The method of claim 1 wherein said coagulation-activating substance is factor Xa.

9. The method of claim 1 wherein said coagulation-activating substance is Russell's viper venom.

10. The method of claim 1 wherein said standard control plasma samples are normal control plasma samples, derived from one or more normal healthy donors, and which contain statistically-common and expected amounts of all known coagulation-related factors.

11. The method of claim 1 wherein at least one of said standard control plasma samples is selected from the group consisting of a protein C-deficient plasma sample and a protein S-deficient plasma sample.

12. The method of claim 1 wherein at least one of said standard control plasma samples is a protein S-deficient plasma sample.

13. The method of claim 1 wherein said vitamin K-dependent coagulation inhibiting protein is protein C.

14. The method of claim 1 wherein at least 1 of said standard control plasma samples is a protein C-deficient plasma sample.

15. The method of claim 1 wherein said method further comprises combining said blood plasma test sample, said coagulation-activating substance, and a cephalin derived from rabbit brain tissue in said calcium-free solution.

* * * * *